United States Patent [19]
Cauwet et al.

[11] Patent Number: 5,961,994
[45] Date of Patent: *Oct. 5, 1999

[54] COSMETIC COMPOSITION CONTAINING AT LEAST ONE NONIONIC SURFACE-ACTIVE AGENT OF THE ALKYL POLYGLYCOSIDES AND/OR POLYGLYCEROLATED TYPE AND AT LEAST ONE CROSSLINKED COPOLYMER OF MALEIC ANHYDRIDE/ ($C_1$-$C_5$) ALKYLVINYL ETHER

[75] Inventors: Danièle Cauwet, Paris; Claude Dubief, Le Chesnay, both of France

[73] Assignee: L'Oreal, Paris, France

[*] Notice: This patent is subject to a terminal disclaimer.

[21] Appl. No.: 08/963,809

[22] Filed: Nov. 4, 1997

Related U.S. Application Data

[63] Continuation of application No. 08/709,664, Sep. 9, 1996, Pat. No. 5,744,147, which is a continuation of application No. 08/607,204, Feb. 26, 1996, abandoned, which is a continuation of application No. 08/214,423, Mar. 18, 1994, abandoned.

[30] Foreign Application Priority Data

Mar. 24, 1993 [FR] France ................................. 93 03403

[51] Int. Cl.$^6$ ........................................................ A61K 7/48
[52] U.S. Cl. ............................... 424/401; 424/59; 424/61; 424/62; 424/69; 424/73; 424/70.2; 424/70.6; 424/70.7; 424/70.11; 424/70.13; 424/78.02; 424/78.03; 424/78.2; 514/844; 514/845; 514/846

[58] Field of Search ................................. 424/401, 59, 61, 424/62, 69, 73, 70.2, 70.6, 70.7, 70.11, 70.13, 78.02, 78.03, 78.2; 514/844, 845, 846

[56] References Cited

U.S. PATENT DOCUMENTS

| | | | |
|---|---|---|---|
| 3,666,671 | 5/1972 | Kalopissis et al. | 252/173 |
| 5,032,391 | 7/1991 | Helioff et al. | 424/11 |
| 5,034,220 | 7/1991 | Helioff et al. | 424/73 |
| 5,057,311 | 10/1991 | Kamegai et al. | 424/10 |

FOREIGN PATENT DOCUMENTS

| | | |
|---|---|---|
| 2139243 | 11/1984 | United Kingdom . |
| WO/9208439 | 5/1992 | WIPO . |

OTHER PUBLICATIONS

"PVM/MA Decadiene Crosspolymer: A New Thickener/Stabilizer", Research Disclosure, No. 3343, Nov. 1992, Emsworth, GB.

*Primary Examiner*—Jyothsna Venkat
*Attorney, Agent, or Firm*—Jacobson, Price, Holman & Stern PLLC

[57] ABSTRACT

The invention relates to a cosmetic composition containing, in a cosmetically acceptable medium, at least one nonionic surface-active agent from the alkyl polyglycoside class and/or one polyglycerolated nonionic surface-active agent and at least one crosslinked copolymer of maleic anhydride/($C_1$–$C_5$)alkyl vinyl ether, as well as to a cosmetic treatment process consisting in applying to keratinous matter a cosmetically effective quantity of this composition.

9 Claims, No Drawings

COSMETIC COMPOSITION CONTAINING AT LEAST ONE NONIONIC SURFACE-ACTIVE AGENT OF THE ALKYL POLYGLYCOSIDES AND/OR POLYGLYCEROLATED TYPE AND AT LEAST ONE CROSSLINKED COPOLYMER OF MALEIC ANHYDRIDE/ ($C_1$-$C_5$) ALKYLVINYL ETHER

This is a continuation of application Ser. No. 08/709,664, filed Sep. 9, 1996, now U.S. Pat. No. 5,146,147 which is a continuation of application Ser. No. 08/607,204, filed Feb. 26, 1996, abandoned, which is a continuation of application Ser. No. 08/214,423, filed Mar. 18, 1994, abandoned.

The invention relates to cosmetic compositions containing at least one nonionic surface-active agent of the alkyl polyglycoside and/or polyglycerolated type and at least one crosslinked copolymer of maleic anhydride/($C_1$–$C_5$)alkyl vinyl ether.

The hydrolysed and neutralized crosslinked copolymer gels of maleic anhydride/($C_1$–$C_5$)alkyl vinyl ether are known as thickening agents or as stabilizing agents in aqueous or anhydrous cosmetic compositions for the care or treatment of hair or skin. They are described in U.S. Pat. Nos. 5,032,391, 5,034,220 and 5,024,779 from the company GAF.

Surface-active agents from the alkyl polyglycoside or polyglycerolated class have already been recommended in washing compositions for hair or skin. They are mild, well-tolerated and biodegradable detergents.

Hair, under attack from atmospheric agents such as light or chemical treatments, and washed with conventional washing bases, is difficult to disentangle, and this disadvantage is even more accentuated in the case of fine hair.

Shampoo compositions which contain only nonionic surface-active agents do not lead to good cosmetic properties; in particular, the disentangling of wet hair is difficult and the hair is coarse.

The applicant has just discovered, surprisingly, that the combination, in washing and/or treating compositions for keratinous matter, of crosslinked copolymers of maleic anhydride/($C_1$–$C_5$)alkyl vinyl ether with specific nonionic surfactants of the alkyl polyglycoside type and/or of the polyglycerolated type imparted considerably improved disentangling properties on these compositions. Moreover, the combination in accordance with the invention makes it possible to obtain a very mild foam, compared to the coarse foam which generally results from the use of nonionic agents.

In addition, the applicant has observed that compositions containing such a combination had good cosmetic properties such as softness and a pleasant feel.

The subject of the present invention is thus cosmetic compositions containing at least one nonionic surface-active agent of alkyl polyglycoside and/or polyglycerolated type and at least one crosslinked copolymer of maleic anhydride/($C_1$–$C_5$)alkyl vinyl ether.

Another subject of the invention consists in the use of these compositions for treating and/or washing keratinous matter such as hair or skin.

Another subject of the invention relates to a process for the cosmetic treatment of hair or of the skin, using compositions in accordance with the invention; the process for washing and treating hair being particularly preferred.

Other subjects of the invention will appear on reading the description and the examples which follow.

The cosmetic compositions according to the invention contain, in a cosmetically acceptable medium, at least one nonionic surface-active agent of alkyl polyglycoside and/or polyglycerolated type and at least one crosslinked copolymer of maleic anhydride/($C_1$–$C_5$)alkyl vinyl ether. The viscosity of an aqueous solution containing from 0.5 to 1.5% by weight of the said hydrolysed and neutralized copolymer, at a pH between 4 and 11, measured at 25° C. using a BROOKFIELD RTV viscometer, with a spindle of the type TE at 10 revolutions/minute, is preferably approximately between 35,000 and 180,000 cps.

The crosslinked copolymers in accordance with the invention are prepared by polymerization of maleic anhydride, an alkyl vinyl ether and a crosslinking agent in the presence of a free radical initiator in a suitable solvent. A mixture of ethyl acetate and cyclohexane (35–55% by weight/45–65% by weight) is preferably used as a solvent.

The crosslinking agents are preferably used in proportions between 1 and 5 mol % relative to the monoalkyl vinyl ether. They are, for example, chosen from unsaturated compounds such as aliphatic diol divinyl ethers; polyethylene glycol divinyl ethers; 1,7-octadiene; 1,9-decadiene; divinylbenzene; N,N'-methylenebisacrylamide; polyethylene glycol diacrylate; trimethylolpropane triacrylate; propylene glycol diacrylate; polyol mono- or diacrylates; triallylamine; tetraallylethylenediamine and diallyl phthalate.

1,7-octadiene or 1,9-decadiene is more particularly used.

The free radical initiators are preferably used in proportions between 0.001 and 1% by weight relative to the monomer composition. They are in particular chosen from azobisisobutyronitrile, benzoyl peroxide, lauroyl peroxide, caprylyl peroxide, acetyl peroxide, acetylbenzoyl peroxide, di-tert-butyl peroxide and azobis(2,4-dimethylvaleronitrile).

The polymerization is carried out at a temperature between 0 and 150° C., preferably between 50 and 100° C., and more particularly between 60 and 80° C.

The crosslinked copolymers thus obtained are in powder form.

When they hydrolysed and neutralized in a basic aqueous solution containing from 0.5 to 1.5% by weight of copolymer and a sufficient amount of a neutralizing agent such as a 10% alkali metal hydroxide solution or a 30% aqueous ammonia solution, or of an alkanolamine such as monoethanolamine, diethanolamine, triethanolamine, aminomethylpropanol or aminomethylpropanediol, the viscosity measured with the BROOKFIELD RTV viscometer, with a spindle of the type TE at 10 revolutions/minute, at 25° C. and at a pH between 4 and 11, and in particular between 6 and 7.4, is preferably between 35,000 and 180,000 cps.

The copolymers which it is preferred to use according to the present invention are maleic anhydride/methyl vinyl ether copolymers crosslinked with 1 to 5 mol %, relative to the methyl vinyl ether, of 1,9-decadiene or of 1,7-octadiene.

An example of a commercially available product of this type is STABILEZE 06 sold by the company ISP.

The crosslinked copolymers of the invention are present in the cosmetic composition in concentrations betwen 0.2 and 5% by weight, and preferably between 0.3 and 3% by weight.

The alkyl polyglycosides which may be used in accordance with the invention correspond in particular to the following formula (II):

$$R(C_6H_{10}O_5)_x\text{—H} \qquad (II)$$

corresponding to the structural formula (III):

$$(III)$$

$$R\text{—O}\left[\begin{array}{c}\text{CH}_2\text{—O}\\\text{O}\\\text{OH}\\\text{OH}\quad\text{OH}\end{array}\right]_x\text{OH}$$

in which: R denotes one or a mixture of alkyl or alkenyl radicals having a straight or branched $C_8$–$C_{24}$ chain; x is a number between 1 and 15.

The alkyl polyglycoside compounds of structural formula (III) defined above, used in accordance with the invention, are preferably represented by the products sold by the company HENKEL under the name APG, such as the products APG 300, APG 350, APG 500, APG 550, APG 625, APG base 10–12; PLANTAREN 300, 600, 1200 CS/UP, 2000 CS/UP; the products sold by the company SEPPIC under the names TRITON CG 110 (or ORAMIX CG 110) and TRITON CG 312 (or ORAMIX NS 10); those sold by the company BASF under the name LUTENSOL GD 70.

The nonionic surface-active agents of the polyglycerolated type, used in accordance with the present invention, are preferably chosen from the following polyhydroxypropyl ether compounds:

(A) The compounds corresponding to the formula (IV):

$$RO[C_3H_5(OH)]_n\text{—H} \qquad (IV)$$

in which the group $[C_3H_5(OH)]$ represents the following structures, taken together or separately:

$$\text{—}\!\!\left(\text{CH}_2\text{CHOH—CH}_2\text{—O}\right)\!\!\text{—} \qquad (IVa)$$

$$\text{—}\!\!\left(\begin{array}{c}\text{CH}_2\text{—CH—O}\\|\\\text{CH}_2\text{OH}\end{array}\right)\!\!\text{—} \quad\text{and} \qquad (IVb)$$

$$\text{—}\!\!\left(\begin{array}{c}\text{CH}_2\text{—CH—O}\\|\\\text{CH}_2\text{OH}\end{array}\right)\!\!\text{—} \qquad (IVc)$$

and R and n have one of the meanings below:

a) R represents one or a mixture of $C_{10}$–$C_{14}$ alkyl radicals and n is a whole or decimal number from 2 to 10, and preferably 3 to 6.

b) R represents a residue:

$$R_2\text{CONHCH}_2\text{—CH}_2\text{OCH}_2\text{—CH}_2\text{—} \qquad (V)$$

where $R_2$ denotes one or a mixture of $C_1$–$C_7$ alkyl and/or alkenyl radicals and n denotes a whole or decimal number from 1 to 5, and preferably from 1.5 to 4.

c) R represents a residue:

$$R_3\text{—CHOH—CH}_2\text{—} \qquad (VI)$$

where $R_3$ denotes a $C_7$–$C_{21}$ aliphatic, cycloaliphatic or arylaliphatic radical and their mixtures, the aliphatic chains in particular denoting alkyl chains which may contain from 1 to 6 ether, thioether and/or hydroxymethylene groups and n denotes a whole or decimal number from 1 to 10.

These surf actants of formula (IV) may be prepared according to the processes described in Patents FR 1,477,048, 2,328,763 and 2,091,516;

(B) The compounds prepared by acid-catalysed condensation of 2 to 10, and preferably of 2.5 to 6, moles of glycidol per mole of alcohol or of alpha-diol containing 10 to 14 carbon atoms, at a temperature of 50 to 120° C., glycidol being added slowly to the alcohol or to the alpha-diol. The process for the preparation of these compounds is described in Patent FR-A-2,169,787;

(C) The polyhydroxypropyl ether compounds prepared by polyaddition of glycerol monochlorohydrin with a polyhydroxylated organic compound in the presence of a strong base, with progressive removal of the water by distillation. These compounds are described in French Patent FR-A-2,574,786.

Among the nonionic surfactants of the polyhydroxypropyl ether class described in paragraphs (A), (B) and (C) above, the preferred compounds are represented by the formulae:

$$(\alpha)\,C_{12}H_{25}O\text{—}\!\!\left(\begin{array}{c}\text{CH}_2\text{—CH—O}\\|\\\text{CH}_2\text{OH}\end{array}\right)_{\!\!4.2}\!\!\text{H} \qquad (VII)$$

$$R_1O\text{—}\!\!\left(\begin{array}{c}\text{CH}_2\text{—CH—O}\\|\\\text{CH}_2\text{OH}\end{array}\right)_{\!\!3.75}\!\!\text{H} \qquad (VIII)$$

where $R_1$ denotes a mixture of $C_{10}H_{21}$ and $C_{12}H_{25}$ alkyl radicals;

($\beta$) the compounds prepared by base-catalysed condensation of 3.5 moles of glycidol with an alpha-diol containing 12 carbon atoms, according to the process described in Patent FR-A-2,091,516;

($\gamma$) the compounds corresponding to the formula:

$$R_2\text{—CONH—CH}_2\text{—CH}_2\text{—O—CH}_2\text{—CH}_2\text{—O}\text{—}\!\!\left(\text{CH}_2\text{—CHOH—CH}_2\text{—O}\right)_{\!\!3.5}\!\!\text{H} \qquad (IX)$$

where $R_2$ denotes a mixture of radicals comprising the following alkyl and alkenyl radicals: $C_{11}H_{23}$, $C_{13}H_{27}$, radicals derived from coconut fatty acids and the radical derived from oleic acid;

($\delta$) the compounds prepared by condensation of 3.5 moles of glycidol with a mixture of $C_{11}$–$C_{14}$ alpha-diols, described in Patent FR-A-2,091,516.

The polyhydroxypropyl ether nonionic surfactant obtained by condensation of glycerol monochlorohydrin (2.5 moles) in the presence of sodium hydroxide with 1,2-dodecanediol is more particularly preferred.

If the compositions according to the invention are not used for washing keratinous matter, the nonionic surface-active agent(s) of alkyl polyglycoside and/or polyglycerolated type is(are) used in such compositions in proportions between 0.1 and 5% by weight relative to the total weight of the composition. These compositions are in particular used as rinsing compositions, which are applied before or after shampooing, colouring, bleaching, a permanent wave or a hair straightening treatment, as a colouring or permanent waving composition.

If the compositions according to the invention are washing compositions, they contain the nonionic surfactant(s) of the alkyl polyglycoside and/or polyglycerolated type in proportions between 5 and 30% by weight relative to the total weight of the composition, and more particularly between 5 and 20% by weight.

The pH of the compositions in accordance with the invention is generally between 2 and 9, more particularly between 3 and 6.

In so far as the cosmetically acceptable medium of the composition according to the invention is an aqueous medium, it may consist exclusively of water or of a mixture of water and a cosmetically acceptable solvent, such as $C_1$–$C_4$ lower alcohols like ethanol, isopropanol and n-butanol; alkylene glycols such as propylene glycol, and glycol ethers.

The compositions according to the invention may take the form of more or less thickened liquids, gels, emulsions (milks or creams), aqueous-alcoholic lotions, dispersions or aerosol foams.

The compositions are, for example, emollient lotions, milks or creams, lotions, milks or creams for the care of keratinous matter, creams or milks for removing make-up, foundation bases, anti-sun lotions, milks or creams, artificial tanning lotions, milks or creams, shaving creams or foams, after-shave lotions, face masks, make-up products for the eyes, make-up powder and foundations for the face, nail varnishes, shampoos, bath or shower products, rinsing compositions for applying before or after shampooing, colouring, bleaching, a permanent wave or a hair straightening treatment.

The compositions in accordance with the invention may in addition optionally contain various additives which do not alter the properties of the compositions, such as anionic, cationic, amphoteric or zwitterionic surface-active agents, nonionic surface-active agents other than those described above, anionic, nonionic, cationic or amphoteric polymers, proteins, hydrocarbon oils such as synthesis oils like iso-paraffins or inorganic, vegetable or animal oils, silicone oils, waxes, resins and/or gums, acidifying or basifying agents, preservatives, active agents, other thickeners, suspension-forming agents, softeners, sunscreen agents, perfumes, biocides, antioxidants, fluorine-containing compounds, pigments or other adjuvants commonly used in cosmetics.

The compositions in accordance with the invention are applied to skin or to hair in a cosmetically effective quantity depending on the nature of the composition.

One specific application of the compositions according to the invention is the application as a composition for the washing and cosmetic treating of keratinous matter, preferably of skin and hair, and more particularly as a a shampoo. In this case, the shampoo is applied to wet or dry hair in effective quantities to wash it, this application being followed by a rinsing.

The examples which follow are intended to illustrate the invention without in any way presenting a limiting character.

EXAMPLE 1

A shampoo is prepared having the following composition:

| | | |
|---|---|---|
| ($C_9$—$C_{10}$—$C_{11}$/20-40-40) alkyl polyglycoside (1,4), sold at a concentration of 50% of AS under the name "APG 300" by the company HENKEL | 10 g | AS |
| Maleic anhydride/methyl vinyl ether copolymer crosslinked with 1,9-decadiene (viscosity of a 0.5% solution: 110,000 cps) | 1.5 g | |
| Triethanolamine lauryl sulphate sold at a concentration of 40% of AS | 5 g | AS |
| Perfume, preservative | qs | |
| Sodium hydroxide | qs | pH = 7 |
| Water | qs 100 g | |

EXAMPLE 2

A shampoo is prepared having the following composition:

| | | |
|---|---|---|
| ($C_9$—$C_{10}$—$C_{11}$/20-40-40) alkyl polyglycoside (1,4), sold at a concentration of 50% of AS under the name "APG 300" by the company HENKEL | 10 g | AS |
| Maleic anhydride/methyl vinyl ether copolymer crosslinked with 1,9-decadiene (viscosity of a 0.5% solution: 50,000 cps) | 1.5 g | |
| Perhydrosqualene | 2 g | |
| Perfume, preservative | qs | |
| Sodium hydroxide | qs | pH = 7 |
| Water | qs 100 g | |

EXAMPLE 3

A rinsing conditioner is prepared having the following composition:

| | | |
|---|---|---|
| ($C_9$—$C_{10}$—$C_{11}$/20-40-40) alkyl polyglycoside (1,4), sold at a concentration of 50% of AS under the name "APG 300" by the company HENKEL | 2 g | AS |
| Maleic anhydride/methyl vinyl ether copolymer crosslinked with 1,9-decadiene, sold under the name "STABILEZE 06" by the company ISP. | 1 g | |
| Heptamethylnonane sold under the name "ARLAMOL HD" by the compnay ICI | 5 g | |
| Preservative, perfume | qs | |
| Sodium hydroxide | qs | pH = 6 |
| Water | qs 100 g | |

EXAMPLE 4

A rinsing conditioner is prepared having the following composition:

| | | |
|---|---|---|
| ($C_9$—$C_{10}$—$C_{11}$/20-40-40) alkyl polyglycoside (1,4), sold at a concentration of 50% of AS under the name "APG 300" by the company HENKEL | 10 g | AS |

| | |
|---|---|
| Maleic anhydride/methyl vinyl ether copolymer crosslinked with 1,9-decadiene (viscosity of a 0.5% solution: 110,000 cps) | 1.75 g |
| Silk protein hydrolysate quaternized with cocyldimethylammonium chloride, sold as an aqueous solution containg 32% of AS under the name "CROSILQUAT" by the company CRODA | 3 g   AS |
| Preservative, perfume | qs |
| Sodium hydroxide | qs   pH = 7 |
| Water | qs 100 g |

EXAMPLE 5

A shampoo is prepared having the following composition:

| | |
|---|---|
| Nonionic poly(hydroxypropyl ether) surfactant prepared by base-catalysed condensation of 3.5 moles of glycidol with a mixture of alphadiols containing 10 to 14 carbon atoms, according to the process described in French Patent No. 2,091,516 | 20 g |
| Maleic anhydride/methyl vinyl ether copolymer crosslinked with 1,9-decadiene (viscosity of a 0.5% solution: 110,000 cps) | 1 g |
| Perhydrosqualene | 2 g |
| Preservative | qs |
| Sodium hydroxide | qs   pH = 5 |
| Water | qs 100 g |

EXAMPLE 6

A shampoo is prepared having the following composition:

| | |
|---|---|
| ($C_9$—$C_{10}$—$C_{11}$/20-40-40) alkyl polyglycoside (1,4), sold at a concentration of 50% of AS under the name "APG 300" by the company HENKEL | 15 g   AS |
| Maleic anhydride/methyl vinyl ether copolymer crosslinked with 1,9-decadiene (viscosity of a 0.5% solution: 50,000 cps) | 1.5 g |
| Polydimethydiphenylsiloxane sold under the name "SILBIONE OIL 70641 V 200" by the company RHONE POULENC | 3 g |
| Preservative | qs |
| Sodium hydroxide | qs   pH = 6 |
| Water | qs 100 g |

EXAMPLE 7

A rinsing conditioner is prepared having the following composition:

| | |
|---|---|
| ($C_9$—$C_{10}$—$C_{11}$/20-40-40) alkyl polyglycoside (1,4), sold at a concentration of 50% of AS under the name "APG 300" by the company HENKEL | 0.2 g   AS |
| Maleic anhydride/methyl vinyl ether copolymer crosslinked with 1,9-decadiene (viscosity of a 0.5% solution: 110,000 cps) | 5 g |
| Rapeseed oil | 3 g |
| Preservative | qs |
| Sodium hydroxide | qs   pH = 4 |
| Water | qs 100 g |

EXAMPLE 8

A hair setting lotion is prepared having the following composition:

| | |
|---|---|
| ($C_9$—$C_{10}$—$C_{11}$/20-40-40) alkyl polyglycoside (1,4), sold at a concentration of 50% of AS under the name "APG 300" by the company HENKEL | 0.1 g   AS |
| Maleic anhydride/methyl vinyl ether copolymer crosslinked with 1,9-decadiene, sold under the name "STABILEZE 06" by the company ISP by the company RHONE POULENC | 1 g |
| Vinylpyrrolidone/vinyl acetate copolymer in alcoholic solution at a concentration of 50% of AS (PVP/VA E 735 from ISP) | 1 g |
| 2-Amino-2-methylpropanol | qs   pH = 7.5 |
| Water | qs 100 g |

EXAMPLE 9

A shower gel is prepared having the following composition:

| | |
|---|---|
| APG 300 | 15 g   AS |
| STABILEZE 06 | 2.5 g |
| Sodium lauryl ether sulphate containing 2.2 moles of ethylene oxide in an aqueous solution containing 28% of AS | 8 g   AS |
| Acrylic acid/dimethyldiallylammonium chloride copolymer (20/80) (Merquat 280 from Merck) | 0.5 g   AS |
| Preservative, perfume | qs |
| NaOH | qs   pH = 6.5 |
| Water | qs 100 g |

We claim:

1. Cosmetic composition, containing, in a cosmetically acceptable medium, 0.1 to 30% by weight, relative to the total weight of the composition, of one or more nonionic alkyl polyglycoside surface-active agent corresponding to the following structural formula:

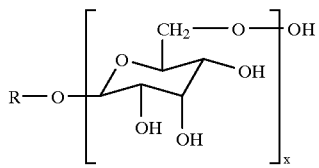

(III)

in which R denotes alkyl radical having a straight or branched $C_8$–$C_{24}$ chain or mixtures thereof and x denotes a number between 1 and 15, and between 0.2 and 5% by weight, relative to the total weight of the composition, of one or more crosslinked copolymer of maleic anhydride/($C_1$–$C_5$) alkyl vinyl ether, which is crosslinked with 1,7-octadiene, the crosslinking agent comprising 1 to 5 mol % relative to the monoalkyl vinyl ether.

2. Composition according to claim 1, wherein the crosslinked copolymer of maleic anhydride/($C_1$–$C_5$)alkyl vinyl ether dissolved in water at a concentration of 0.5 to 1.5%, which copolymer is hydrolysed and neutralized at a pH between 4 and 11, has a viscosity of approximately between 35,000 and 180,000 cps, measured at 25° C. with a BROOKFIELD RTV viscometer, with a spindle of the type TE at 10 revolutions/minute.

3. Composition according to claim 1, wherein the cosmetically acceptable medium is an aqueous medium which consists exclusively of water or of a mixture of water and a cosmetically acceptable solvent.

4. Composition according to claim 1, wherein it is in it takes the form of a thickened liquid, a gel, an emulsion, an aqueous-alcoholic lotion, a dispersion or an aerosol foam.

5. Composition according to claim 1, further comprising anionic, cationic, amphoteric or zwitterionic surface-active agents, anionic, nonionic, cationic or amphoteric polymers, proteins, hydrocarbon oils, silicone oils, waxes, resins or gums, acidifying or basifying agents, preservatives, active agents, other cosmetic thickeners, suspension-forming agents, softeners, sunscreen agents, perfumes, biocides, antioxidants, fluorine-containing compounds, pigments or other adjuvants.

6. Cosmetic treatment process, comprising applying to skin or to hair a cosmetically effective quantity of a composition according to claim 1.

7. Process for washing and cosmetically treating hair, comprising applying to wet or dry hair an effective quantity of the composition as described in claim 1 to wash the hair, and then rinsing with water.

8. Composition according to claim 1, wherein it contains between 0.3 and 3% by weight, relative to the total weight of the composition, of crosslinked copolymer.

9. Composition according to claim 1, wherein it contains 5 to 20% by weight, relative to the total weight of the composition, of the nonionic surface-active agent.

* * * * *